US005552319A

United States Patent [19]
Yang et al.

[11] Patent Number: 5,552,319
[45] Date of Patent: Sep. 3, 1996

[54] APPARATUS AND METHOD FOR MONITORING AND CONTROLLING BIOLOGICAL ACTIVITY IN WASTEWATER AND CONTROLLING THE TREATMENT THEREOF

[75] Inventors: Xin Yang, Holland; Jaw F. Lee, Berwyn; Sergey K. Maneshin, Upper Holland; Marcus E. Kolb, Phoenixville, all of Pa.

[73] Assignee: BioChem Technology, Inc., King of Prussia, Pa.

[21] Appl. No.: 248,767

[22] Filed: May 25, 1994

Related U.S. Application Data

[63] Continuation-in-part of Ser. No. 208,020, Mar. 8, 1994, Pat. No. 5,466,604, which is a continuation-in-part of Ser. No. 95,123, Jul. 20, 1993, Pat. No. 5,401,412.

[51] Int. Cl.[6] .................................................... C12M 1/34
[52] U.S. Cl. .................................. 435/286.5; 435/286.7; 435/287.1
[58] Field of Search ........................... 435/286.1, 286.5, 435/286.6, 286.7, 287.1, 810

[56] References Cited

U.S. PATENT DOCUMENTS

| | | | |
|---|---|---|---|
| 3,760,829 | 9/1973 | Schuk et al. | 137/93 |
| 3,925,721 | 12/1975 | Petroff | 324/0.5 R |
| 3,926,737 | 12/1975 | Wilson et al. | 195/108 |
| 4,246,101 | 1/1981 | Selby, III | 210/615 |
| 4,260,490 | 4/1981 | Moss et al. | 210/620 |
| 4,564,453 | 1/1986 | Coplot et al. | 210/614 |
| 4,631,530 | 12/1986 | Gasper | 340/679 |
| 4,999,116 | 3/1991 | Bowers | 210/709 |
| 5,013,442 | 5/1991 | Davis et al. | 210/614 |
| 5,094,752 | 3/1992 | Davis et al. | 210/614 |
| 5,173,187 | 12/1992 | Nader et al. | 210/614 |
| 5,180,494 | 1/1993 | Yamaguchi et al. | 210/603 |
| 5,466,604 | 11/1995 | Yang et al. | 435/286.1 |

FOREIGN PATENT DOCUMENTS

| | | |
|---|---|---|
| 662-579 | 5/1979 | U.S.S.R. . |
| WO90/10083 | 7/1990 | WIPO . |
| WO93/23738 | 11/1993 | WIPO . |

OTHER PUBLICATIONS

G. T. Daigger, J. A. Buttz and J. P. Stephenson, *Analysis of Techniques for Evaluating and Optimizing Existing Full–Scale Wastewater Treatment Plants* Wat. Sci. Tech. vol. 25, No. 4-5, pp. 103–118, 1992.

A. R. Howgrave–Graham, F. M. Wallis & P. L. Steyn, *A Bacterial Population Analysis of Granular Sludge from an Anaerobic Digester Treating a Maize–Processing Waste* Bioresource Technology 37 (1991) 149–156.

G. Holm Kristensen, P. Elberg Jørgensen and M. Henze, *Characterization of Functional Microorganism Groups and Substrate in Activated Sludge and Wastewater by Aur, Nur and Our* Wat. Sci. Tech. vol. 25, No. 6, pp. 43–57, 1992.

Tomonori Matsuo, Takashi Mino and Hiroyasu Sato, *Metabolism of Organic Substances in Anaerobic Phase of Biological Phosphate Uptake Process* Wat. Sci. Tech. vol. 25, No. 6, pp. 83–92, 1992.

Ma. del Carmen Doria–Serrano, S. González–Martínez and M. Hernández–Esparza, *Biochemical Models for Phosphate Accumulating Microorganisms* Wat. Sci. Tech. vol. 26, No. 9–11, pp. 2245–2248, 1992.

H. Spanjers and A. Klapwijk, *Continuous Estimation of Short Term Oxygen Demand from Respiration Measurements* Wat. Sci. Tech. vol. 24, No. 7, pp. 29–32, 1991.

George Hassapis, *Biological Oxygen Demand (BOD) Monitoring by a Multiprocessing System* IEEE Transactions on Instrumentation and Measurement, vol. 40, No. 6, Dec. 1991.

D. Jenkins and V. Tandoi, *The Applied Microbiology of Enhanced Biological Phosphate Removal—Accomplishments and Needs* Wat. Res. vol. 25, No. 12, pp. 1471–1478, 1991.

S. Ghekiere, H. Bruynooghe, K. Van Steenbergen, L. Vriens, A. Van Haute and H. Verachtert, *The Effects of Nitrates and Carbon Compounds on Enhanced Biological Phosphorus Removal from Wastewaters* European Water Pollution Control, vol. 1, No. 4, 1991.

A. Grabińska–Loniewska, *Denitrification Unit Biocenosis* Wat. Res. vol. 25, No. 12, pp. 1565–1573, 1991.

*Primary Examiner*—David A. Redding
*Attorney, Agent, or Firm*—Miller & Christenbury

[57] ABSTRACT

Apparatus which monitors and controls biological activity of wastewater under anaerobic, anoxic and aerobic conditions by measuring changes in dissolved oxygen content of the wastewater and/or cellular NADH. A wastewater treatment system is controlled in accordance with the results generated by the monitoring system.

20 Claims, 10 Drawing Sheets

APPARATUS AND METHOD FOR MONITORING AND CONTROLLING BIOLOGICAL ACTIVITY IN WASTEWATER AND CONTROLLING THE TREATMENT THEREOF

This is a continuation-in-part of application Ser. No. 08/208,020, filed Mar. 8, 1994 now U.S. Pat. No. 5,466,604 which is a continuation-in-part of application Ser. No. 08/095,123, filed Jul. 20, 1993 now U.S. Pat. No. 5,401,412.

FIELD OF THE INVENTION

The present invention relates to apparatus and methods for monitoring and controlling biological activity in wastewater and controlling the treatment thereof, and more particularly to apparatus and methods for real time monitoring the quantity of dissolved oxygen in activated sludge used in a wastewater treatment process and using the results of such monitoring to control selected aspects of the treatment process.

BACKGROUND OF THE INVENTION

The prior art has employed many devices and systems to process and purify water from industrial operations and municipal sources prior to discharging the water. Activated-sludge wastewater treatment plants (WWTP's), which are well known in the art, have been most often utilized to address this problem. Additionally, many industrial and municipal water treatment plants utilize biological systems to pre-treat their wastes prior to discharging into the usual municipal treatment plant. In these processes, the microorganisms used in the activated sludge break down or degrade contaminants for the desired water treatment. Efficient process performance and control requires quick and accurate assessment of information on the activity of microorganisms. This has proven to be a difficult task in view of the wide variety of materials and contaminants that typically enter into treatment systems. Variations in the quantity of wastewater being treated, such as daily, weekly or seasonal changes, can dramatically change numerous important factors in the treatment process, such as pH, temperature, nutrients and the like, alteration of which can be highly detrimental to proper wastewater treatment. Improperly treated wastewater poses serious human health dangers.

Various biological nutrient removal (BNR) processes are currently used in wastewater treatment plants to assist in contamination degradation. In a typical BNR process, contaminants in the wastewater, such as carbon sources (measured as biological oxygen demand or BOD), ammonia, nitrates, phosphates and the like are digested by the activated sludge in anaerobic, anoxic and aerobic stages, also known in the art. In the anaerobic stage, the wastewater, with or without passing through a preliminary settlement process, is mixed with return activated sludge (RAS), sometimes hereinafter referred to as "mixed liquor."

Certain microorganisms in the RAS are capable of rapid uptake of readily biodegradable carbon sources, such as short chain fatty acids and of forming storage products such as poly-β-hydroxybutyrate (PHB) and poly-β-hydroxyvalate (PHV). Energy for this process is provided by the hydrolysis of intracellular polyphosphates. As a result of an anaerobic selector, a large portion of available carbon sources are removed by poly-P forming microorganisms, and $PO_4^{-3}$ is released into the water phase. The rapid uptake and storage of carbonaceous substrates by poly-P forming species of microorganisms insures proper phosphate removal in later oxic processes. It also denies access of other competing organisms to the limited amount of substrates available in the wastewater under anaerobic conditions.

In most wastewater treatment plants, one or several anoxic stages are arranged in the BNR process. In the anoxic stage, denitrifiers, i.e., microbial species capable of denitrification, utilize nitrate and/or nitrite as electron acceptors and consume some of the available carbon sources during the denitrification process. $NO_x$ is reduced stepwise to nitrogen gas and released to the atmosphere in the following manner:

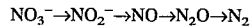

$$NO_3^- \to NO_2^- \to NO \to N_2O \to N_2$$

The nitrate is usually supplied by recycling a certain volume of wastewater at the end of the oxic stage back to the beginning of the anoxic stage.

One or several oxic stages are typically employed in BNR processes. In the oxic stage, air containing about 20% oxygen or pure oxygen, is supplied so that a desired dissolved oxygen level is maintained. Autotrophic nitriflers, i.e., microbial species capable of using ammonia as their energy source, convert ammonia to nitrite and nitrate under aerobic conditions. Poly-P microbial species in the wastewater uptake phosphate from the water phase and digest their intracellular PHB and PHV storage products converting it into polyphosphate, a compound for energy storage. The polyphosphate pool of the poly-P microbial species is thus replenished and phosphorous is removed from the water phase. The phosphorous is then removed from the system by sludge wasting, which is well known in the art. Under aerobic conditions, the remaining carbon sources in the water phase are further digested by aerobic organisms.

However, it has been difficult to properly coordinate the many variables effecting the process in a manner to operate the treatment process at minimal cost and maintain desired and, sometimes, required treatment standards.

OBJECTS OF THE INVENTION

It is an object of the present invention to provide apparatus for monitoring biological activity in wastewater treatment systems during the oxic stages to maximize the efficiency of the treatment process.

It is a further object of the present invention to provide apparatus for real-time monitoring of the purification of wastewater to enhance control of the anaerobic, anoxic and/or oxic stages of a wastewater treatment process, to maximize process performance in response to transient and other conditions.

Other objects of the present invention will be apparent to those of ordinary skill in the art based on the following detailed description of preferred embodiments and the appended claims.

SUMMARY OF THE INVENTION

In accordance with the invention, the apparatus monitors and controls biological activity of wastewater under aerobic or oxic conditions by measuring changes in dissolved oxygen content of the wastewater. The quantity of dissolved oxygen in the wastewater changes as a result of metabolic activity of the microorganisms in the wastewater. The corresponding change in dissolved oxygen (hereinafter sometimes referred to as "D.O.") is detected and then registered by a monitoring system, such as a real time on-line computer data acquisition system, which analyzes the changes and evaluates the biological activity of the wastewater. The monitoring system then determines the changes in operating parameters necessary for the wastewater system to maximize the performance of the BNR processes.

A sample of the wastewater is pumped from a bioreactor tank into an in situ chamber monitored by a D.O. detector in the process. The sample is agitated to ensure uniform distribution of the wastewater and differences in D.O. of the wastewater are registered and analyzed by the monitoring system. The sample is then returned to the bioreactor tank and the wastewater treatment system is controlled in accordance with the results generated by the monitoring system. Detection and monitoring of D.O. may be used in conjunction with other biological activity detecting and monitoring apparatus to assist in control of all or a part of the aerobic, anoxic or oxic stages of the wastewater treatment process.

DETAILED DESCRIPTION OF THE INVENTION

Figure 1:
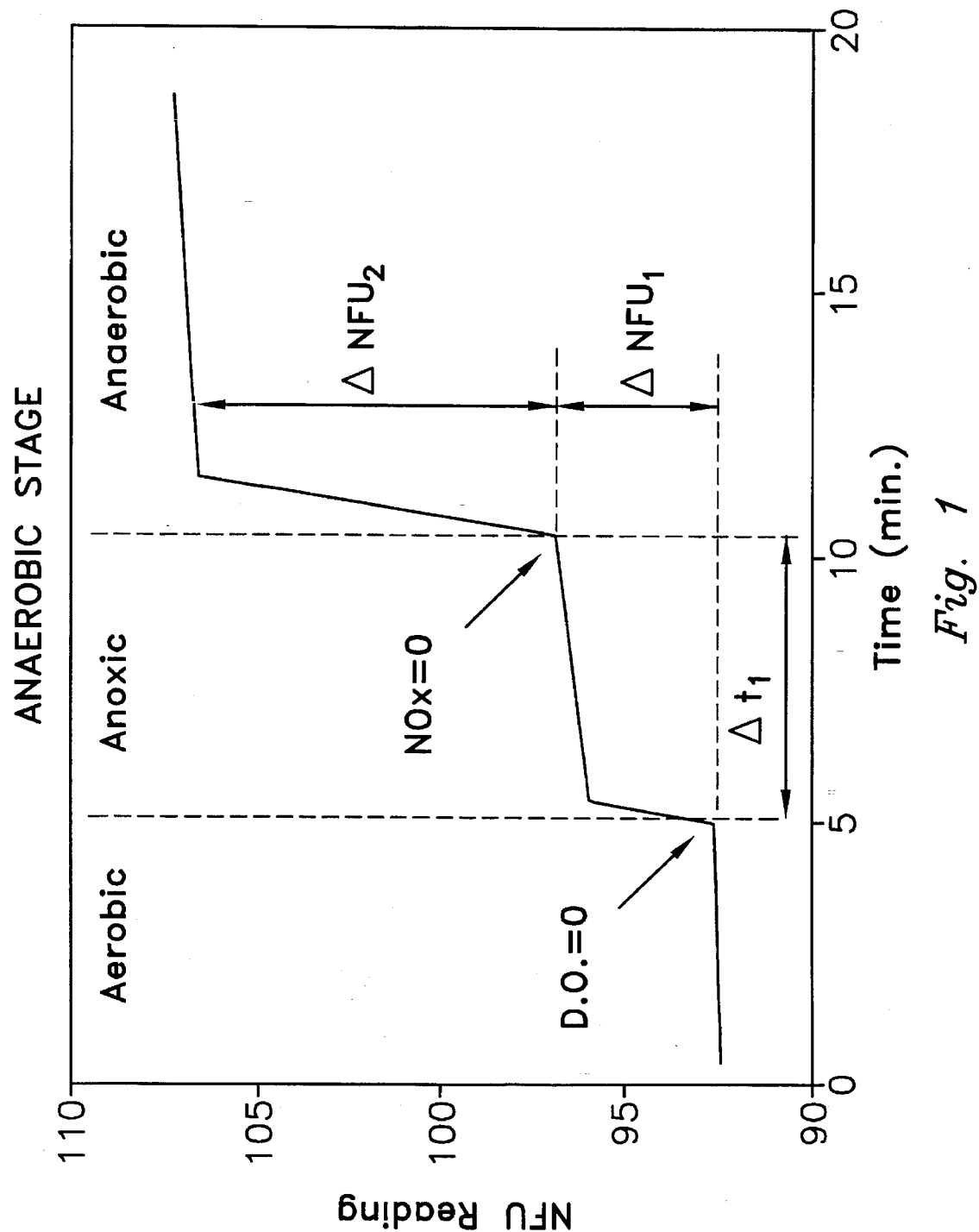
FIG. 1 is a graph of an operational profile depicting changes in biological activity, measured by fluorescence, over time from an anaerobic stage of treatment.

The proper evaluation and control of a complex BNR process requires an accurate and current assessment of the metabolic activity of the wastewater in a variety of environments and under a number of conditions. Unlike oxygen metabolism, which is active during the aerobic stage of the BNR process, NADH metabolism is involved in all environmental stages. Thus, NADH is an excellent indicator of metabolic activity that can be used to control the entire BNR process. Oxygen metabolism also plays an important role in controlling portions of the BNR, which can be further enhanced when taken in conjunction with NADH metabolism. The dominant organisms and the active biochemical pathways vary with the environmental stages of the bioreactor. However, one common factor is the requirement to transfer energy by the oxidization of available energy sources.

It is generally believed that under anaerobic conditions, organic materials such as acetate, for example, are taken up by the cells and converted to acetyl-CoA with the energy for the conversion coming from hydrolysis of intracellular polyphosphate. Acetyl-CoA is further converted to PHB for storage. The reducing power in the form of NADH required for this conversion is obtained by circulating some of the acetyl-CoA through a tricarboxylic acid (TCA) cycle. Also, there may be alternate sources of NADH responsible for this anaerobic conversion of acetyl-CoA to PHB. The concentration of NADH is determined by the balance between the rates of reduction (generation) and oxidization (consumption) reactions. The oxidizing power of the organic compounds involved in the oxidization of NADH in an anaerobic fermentation is much weaker than those of nitrate and oxygen in anoxic and aerobic processes. For example, the reduction potential for the oxidization-reduction pair of pyruvate/lactate is $-0.19$ V while those for $NO_3^-/N_2$ and $1/2\ O_2/H_2O$, are $+0.74V$ and $+0.82$ V, respectively. Consequently, the rate of NADH oxidization is much slower with anaerobic metabolism than with denitrification and respiration. The intracellular level of NADH at the anaerobic stage is therefore higher than those at the anoxic and oxic stages.

In order to effectively control operation of the BNR process, it is necessary to regulate specific process parameters based upon the biological activity of the microorganisms in the anaerobic, anoxic and oxic stages of the treatment. Wastewater treatment plants are often subjected to severe transient conditions, such as diurnal variations in organic loads. Controlling the treatment process in response to these conditions requires a fast and effective means of measuring biological activity. Equipment is provided in a typical WWTP which permits such process control. For example, process parameters controlled by such equipment include rate of input of primary effluent, rate of input of return activated sludge, rate of denitrification recycle, types and quantity of microorganisms, number and location of anaerobic, anoxic and aerobic stages, residence times, nutrient type and introduction rate, air or oxygen purity and introduction rate, pH, temperature and the like.

The invention is directed towards an improved apparatus for monitoring and controlling biological activity in wastewater treatment systems by detecting, among other things, changes in fluorescence and in the dissolved oxygen in the wastewater. The apparatus includes a chamber which is opened and closed to capture a sample of wastewater. The chamber contains at least a dissolved oxygen probe and preferably also a fluorescence detector which detect changes in the biological activity as the wastewater shifts its metabolism due to changes in environmental conditions. These real-time changes in biological activity may be monitored and can be used as the input function for driving process and control algorithms to ensure efficient process performance. Such algorithms are known in the art and are not discussed further. It should be noted that the following embodiments of the present invention are for the purpose of illustration only and are not intended to limit the spirit or scope of the invention as defined in the appended claims in any way.

Figure 5:
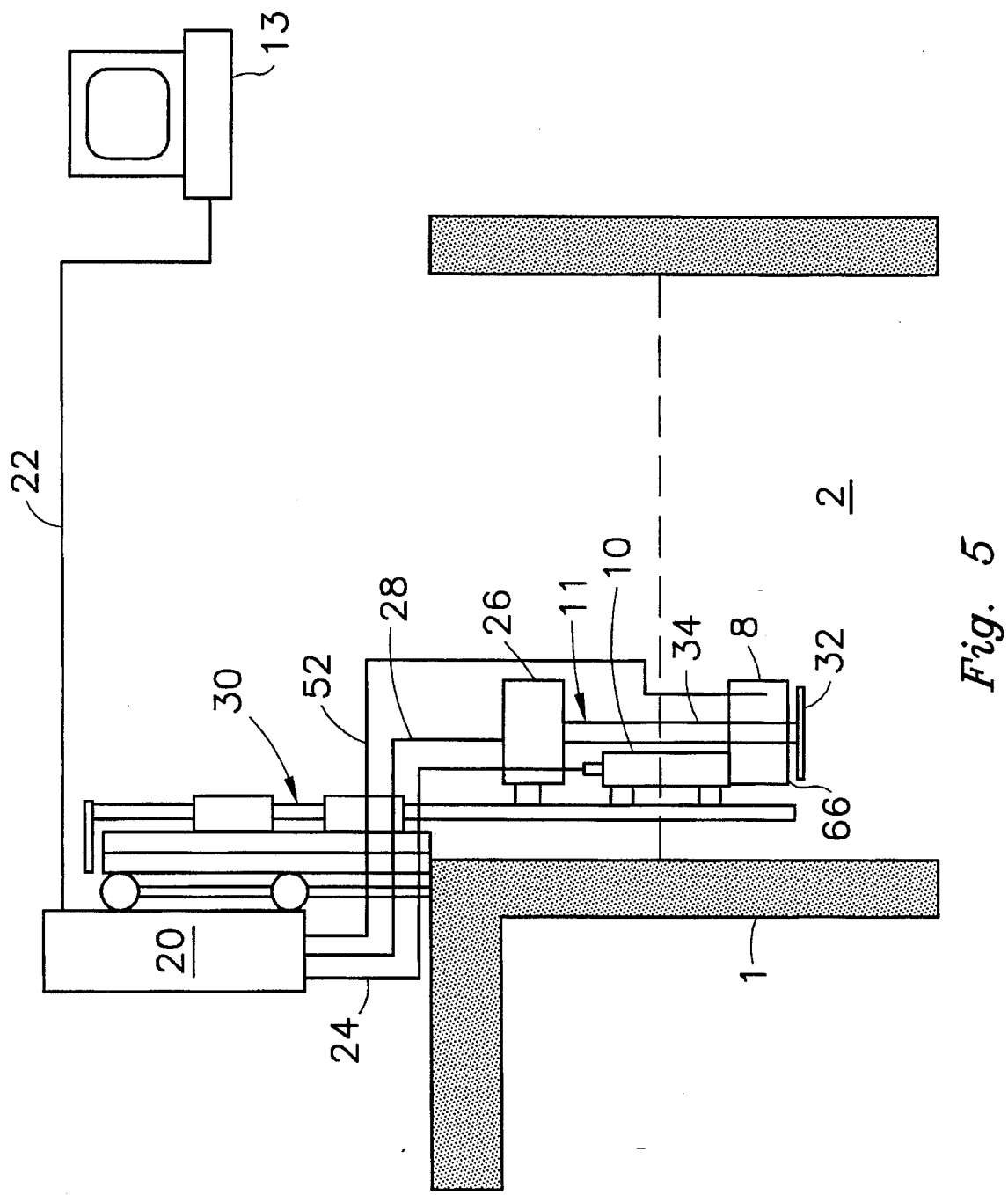
FIG. 5 shows a schematic front elevational view of one embodiment of apparatus of the invention used to detect and monitor dissolved oxygen or fluorescence in a bioreactor tank.

One embodiment of apparatus for sampling wastewater is shown in FIG. 5. A bioreactor tank 1 (or alternatively a wastewater channel) contains wastewater 2 and sludge. Detection apparatus is mounted on the top of bioreactor tank 1 and extends into wastewater 2. The apparatus includes a central control unit 20 connected to a computer/monitor 13 by wire or wireless connection 22. Similarly, central control unit 20 connects to detection probe 10 by way of wire connection 24. Motor container 26 also connects to central control unit 20 by way of connection wire 28. Power is supplied to motor container 26 also by wire connection 28.

Detection probe 10 is positioned in detection chamber 8 and electrically connected to computer/monitor 13 to detect changes in the quantity of dissolved oxygen or changes in fluorescence emitted by microorganisms in the wastewater sample. A preferred dissolved oxygen detection probe 10 is manufactured by Yellow Spring Instrument. It is also possible for probe 10 to be a fluorescence detection probe. A preferred fluorescence detection probe 10 known as FLUO-ROMEASURE® is manufactured by the assignee herein and disclosed in U.S. Pat. No. 4,577,110. Of course, other apparatus can be employed as probes so long as the same or similar detection capabilities are available. Computer/monitor 13 may be of any suitable type such as a personal computer or the like. Feeding device 52, also connected to computer/monitor 13, provides nutrients or oxygen or other reactants to the microorganisms in the wastewater in detection chamber 8.

Figure 6:
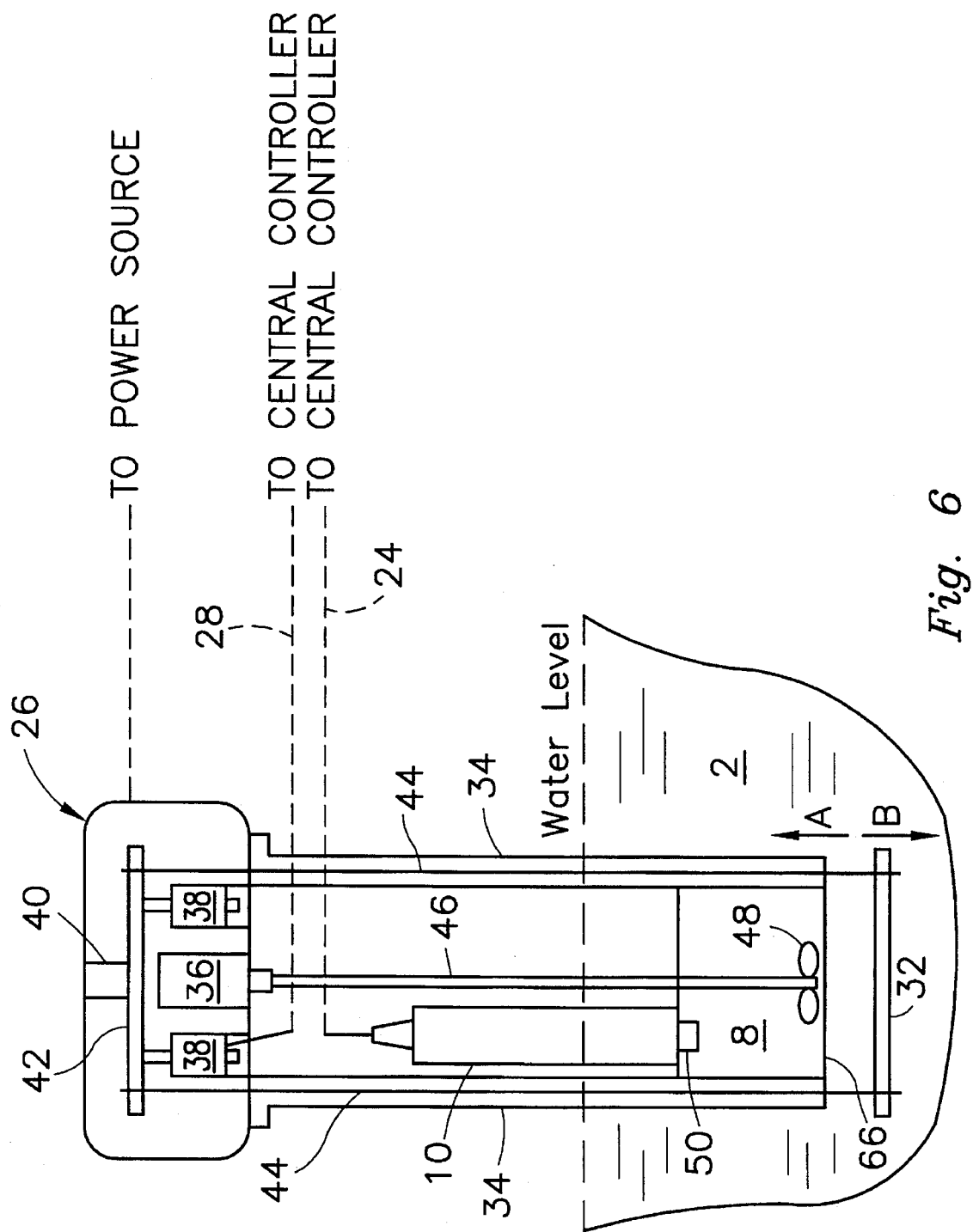
FIG. 6 shows an exploded schematic view, partially taken in section, of wastewater sampling apparatus from FIG. 5.

Sampling unit 11 is mounted onto a movable carriage 30 which is capable of moving substantially vertically upwardly and downwardly to move detection probe 10 into and out of wastewater 2. The precise structure of movable carriage 30 is not critical so long as movability of sampling unit 11 is achieved. Detection probe 10 has its detection end 50 located in detection chamber 8 (as shown in FIG. 6). Detection chamber 8 has an opening 66 and an adjacent movable cover 32 which moves vertically upwardly and downwardly along guide channels 34 and closes or seals opening 66.

FIG. 6 shows an exploded view of one specific construction of sampling unit 11. Motor container 26 includes gear motor 36, solenoid pullers 38 and spring 40 connected to connecting bar 42. Connecting bar 42 also connects to guide rods 44 which extend through guide channels 34. Guide rods 44 terminate on their other end at movable cover 32. Gear motor 36 connects to propeller rod 46 which connects to propeller 48. Propeller 48 is located interiorly of detection chamber 8 which also contains detection end 50.

Figure 7:
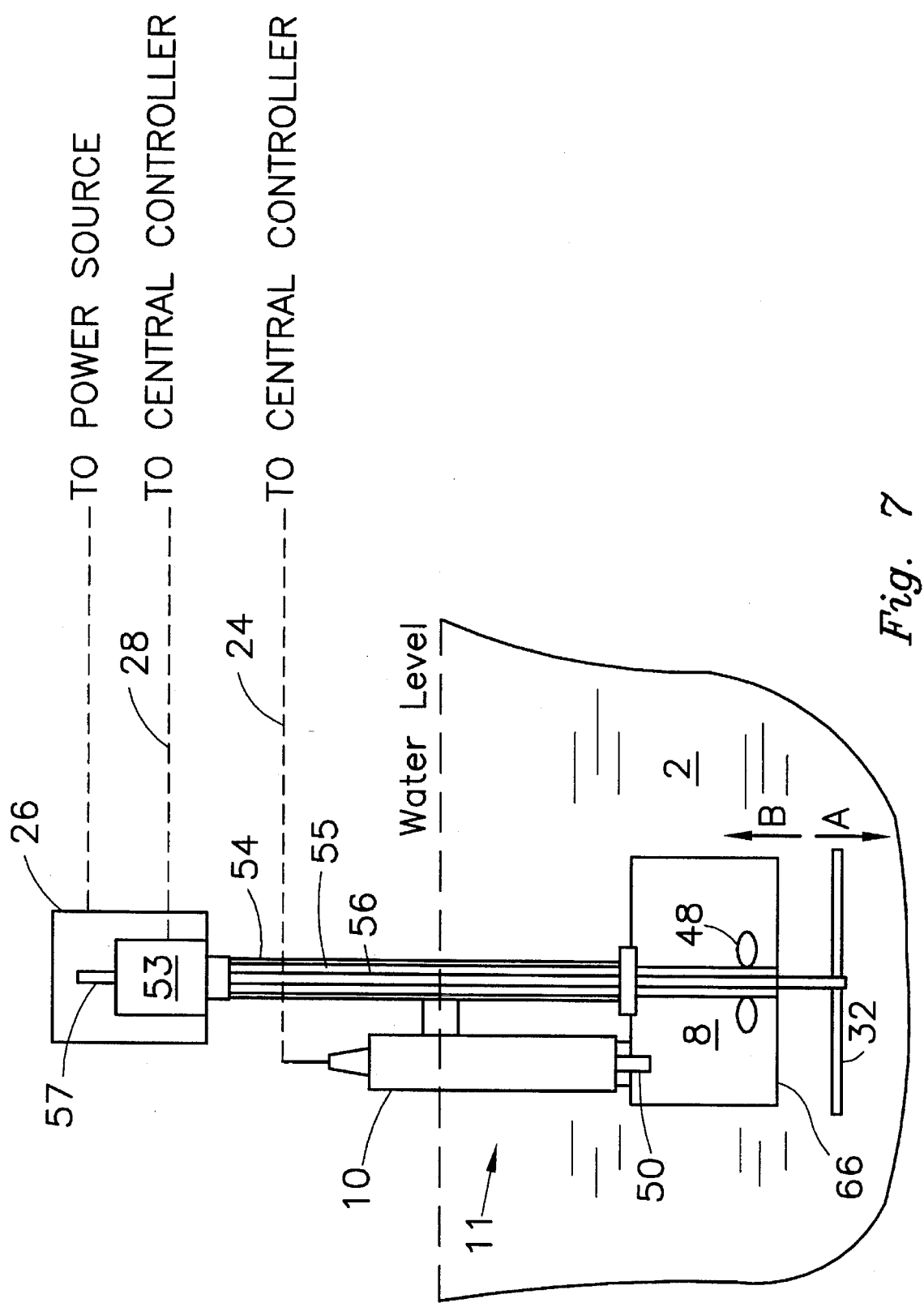
FIG. 7 shows an exploded schematic view, partially taken in section, of another embodiment of the apparatus shown in FIGS. 5 and 6.

FIG. 7 shows an exploded view of another specific construction of a sampling unit 11. Motor container 26 includes linear actuator 53 which connects to a central controller by way of connection wire 28. The linear actuator 53 drives a threaded shaft 57 which connects to inner shaft 56, which extends through outer shaft 55. The assembly formed from inner and outer shafts 56 and 55, respectively, is shielded by stainless steel pipe 54. Pipe 54 connects to chamber 8 which contains propeller 48 and receives detection end 50 of detection probe 10 which connects to the central controller by way of wire connection 24. Detection chamber 8 has an opening 66 which may be closed/sealed with movable cover 32, which connects to inner shaft 56.

The apparatus shown in FIGS. 5 and 6 preferably operates as follows. When it is desired to sample a portion of wastewater, a control signal is sent to solenoid pullers 38 via connection wire 28, which together apply a force to connecting bar 42 and push guide rods 44 and movable cover 32 in the direction of arrow "B", working against the pulling action of spring 40. Detection chamber 8 is then in an open position. Rotation of propeller 48 causes wastewater positioned interiorly of chamber 8 to move outwardly of the chamber and into the body of wastewater 2 and portions of the body of wastewater 2 outside of chamber 8 to move inwardly of detection chamber 8, thereby flushing detection chamber 8 and supplying a fresh quantity of wastewater for sampling.

After a fresh sample is taken into detection chamber 8, the control signal to solenoid pullers 38 is cut off, thereby releasing the pushing force of solenoid pullers 38. Spring 40 returns to its normal position, pulling connecting bar 42, guide rods 44 and movable cover 32 in the direction of arrow "A" and chamber 8 is then in a closed/sealed position.

After filling detection chamber 8 with a fresh sample of wastewater, the metabolic activity of the sample changes such as from an aerobic to an anoxic to an anaerobic condition as time elapses. The time intervals that the sample spends in various states, such as the aerobic, anoxic and anaerobic states, and the changes in fluorescence and dissolved oxygen concentration corresponding to changes in metabolic activity, may be detected by probe 10 depending on whether it is a dissolved oxygen probe or a fluorescence probe, registered and analyzed by computer 13. Use of computer 13 allows for the real-time, on-line monitoring of the biological activity in detection chamber 8. Interpretation of the information obtained by the present invention depends on its specific application and installation location in the WWTP. The design of the apparatus may be modified to meet the specific requirements of the wastewater treatment plant and its location. Upon completion of sample analysis, the central controller actuates solenoid pullers 38 which permits downward movement of movable cover 32 in the direction of arrow "B". This opens detection chamber 8 again for further flushing and uptake of a new sample.

Still another embodiment of sampling apparatus of the invention is shown in FIG. 7. The movable cover 32 and propeller 48 are driven by the same reversible low RPM motor 53 which coaxially connects inner shaft 56 and outer shaft 55. The coaxial assembly is shielded by stainless steel pipe 54. When it is desired to sample a portion of wastewater, a control signal is sent to motor 53, which changes the direction of rotation at the command. Movable cover 32 is pushed in the direction of arrow "B" by inner shaft 56 driven by an ACME shaft 57 connected to motor 53. At the open position, rotation of propeller 48 forces an exchange of wastewater between the inside and outside of detection chamber 8 and detection chamber 8 is filled with a fresh sample of wastewater. After a given period of time, e.g. 30 seconds, motor 53 is programmed to reverse its rotation direction, movable cover 32 is pulled in the direction of arrow "A" until detection chamber 8 is fully closed or sealed.

The fresh wastewater sample is analyzed in the same manner as described with respect to FIG. 6. Upon completion of sample analysis, the central controller reverses the direction of motor 53, which pushes the movable cover 32 to the open position again for further flushing and uptake of a new sample.

Figure 8:
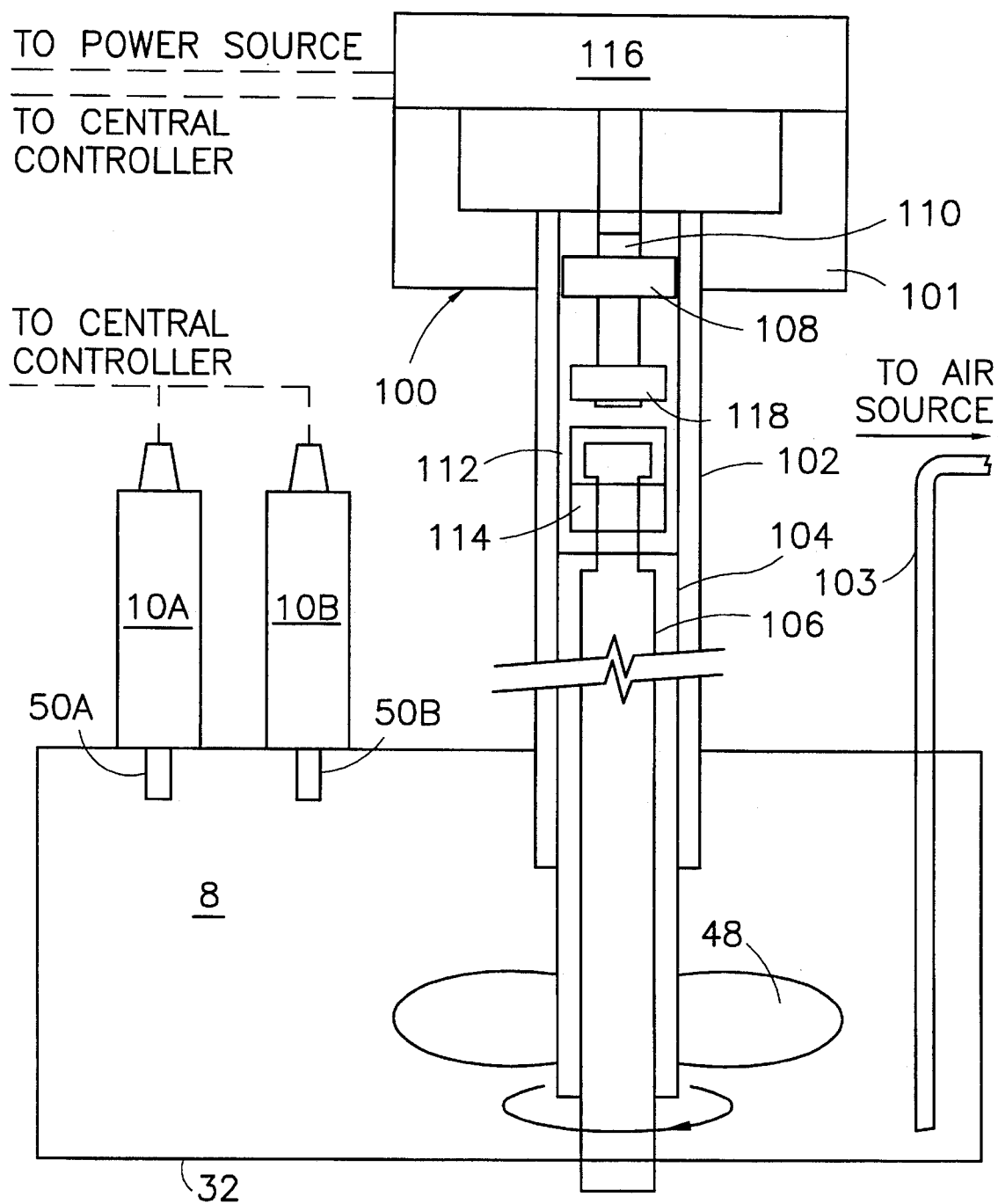
FIG. 8 shows a schematic front elevational view of another embodiment of the invention used to detect and monitor dissolved oxygen and/or fluorescence of a bioreactor tank, the tank being in a closed position.
Figure 9:
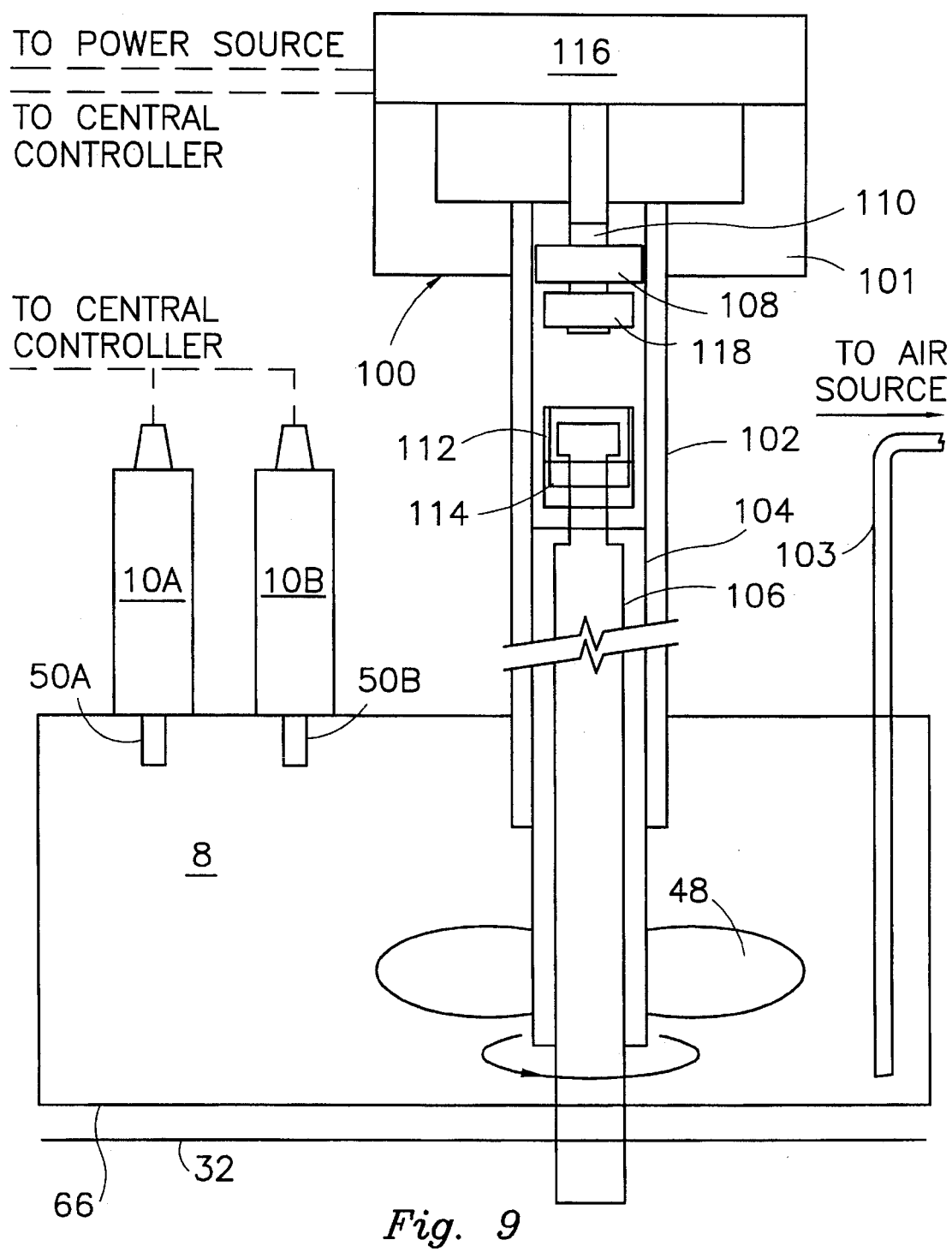
FIG. 9 shows a schematic front elevational view of the apparatus shown in FIG. 8 with the tank in an open condition.

FIG. 8 shows another embodiment of the invention wherein detection chamber 8 has a detection probe 10A with a detection end 50A. Detection probe 10A is a dissolved oxygen probe. Detection chamber 8 also has a detection probe 10B with a detection end 50B. Detection probe 10B is a fluorescence probe. Propeller 48 is located interiorly of detection chamber 8. Cover 32 is in a closed position which covers opening 66 (as shown in FIGS. 7 and 9). An air diffuser 103 is located on the inside of chamber 8 and connects to an air or oxygen source.

Propeller 48 is connected to motor container 100 by way of a series of coaxial tubes 102, 104 and 106. A nut 108 and a thrust bearing sleeve 112 are contained in and attached to middle tube 104. Outside tube 102 is mounted to base 101. Nut 108 is axially movable along threaded rod 110 to either open or close cover 32 depending on motor direction of motor 116. Nut 108 travels axially only if induced drag on middle tube 104 exceeds an amount of torque required for nut 108 to turn on threaded rod 110. This drag can be induced by propeller 48 attached to middle tube 104 and/or any bushings or other hardware in contact with middle tube 104. Thrust bearing sleeve 112 holds bearing 114 which carries axial tension of central tube 106 when cover 32 is closed. Bearing 114 allows middle tube 104 to rotate independently of central tube 106 and transfers axial motion of middle tube 104 to central tube 106. Outside tube 102 supports both motor container 100 and chamber 8 while protecting the internal parts. Chamber 8 is substantially sealed to outside tube 102 and when cover 32 is pulled against chamber 8 the space inside chamber 8 is sealed.

When motor 116 rotates in one direction nut 108 travels away from the motor, pushing cover 32 open. When nut 108 reaches stop 118, nut 108 no longer travels axially and this causes middle tube 104 to substantially match the motor speed. Chamber 8 is then in an open condition and propeller 48 induces an exchange of fluid between the inside and outside of chamber 8, as shown in FIG. 9.

When motor 116 and threaded rod 110 rotate in the opposite direction nut 108 travels toward the motor, pulling cover 32 closed. When chamber 8 is closed, axial motion of nut 108 is prevented by tension on nut 108. This causes middle tube 104 to rotate at the same speed as motor 116 and threaded rod 110. Chamber 8 is then in a closed position so that fluid is retained inside chamber 8 while being constantly mixed by propeller 48, as shown in FIG. 8.

Figure 10:
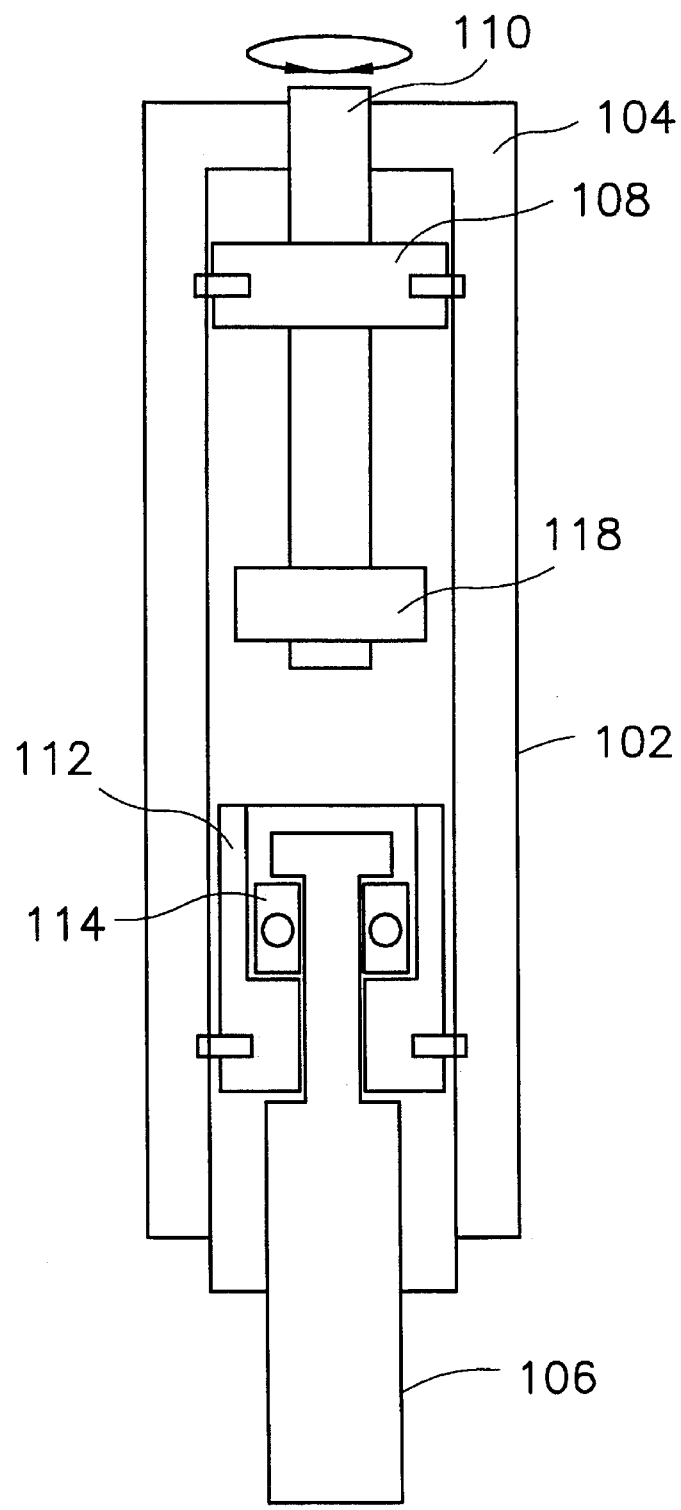
FIG. 10 shows an exploded schematic view, partially taken in section, of a portion of the apparatus shown in FIGS. 8 and 9.

FIG. 10 shows an exploded view of the various drive components shown in FIGS. 8 and 9:

Threaded rod 110 is fixed to reversible motor 116 and prevented from axial travel. This induces linear travel in middle tube 104 only when middle tube 104 offers a rotational resistance greater than torque required to move nut 108 along threaded rod 110. The rotational speed of middle tube 104 must equal the rotational speed of the motor when middle tube 104 is prevented from moving axially. This occurs when chamber 8 is closed or when nut 108 reaches lower stop 118.

Middle tube 104 moves along its longitudinal axis to open and close chamber 8. It rotates in one direction when open and in the opposite direction when closed. Stop attaches to threaded rod 110 and prevents nut 108 from linear travel beyond threaded rod 110 length. Outer tube 102 acts as protective sheath and is in compression when cover 32 is closed. Central tube 106 is attached to cover 32. It rotates independently of middle tube 104 but moves axially with middle tube 104. Thrust bearing sleeve 112 holds bearing 114 and is attached to middle tube 104. It allows middle tube 104 to rotate independently of central tube 106 and transfers axial motion from middle tube 104 to central tube 106. Bearing 114 takes axial tension of central tube 106 and allows middle tube 104 to rotate independently of central tube 106.

Figure 4:
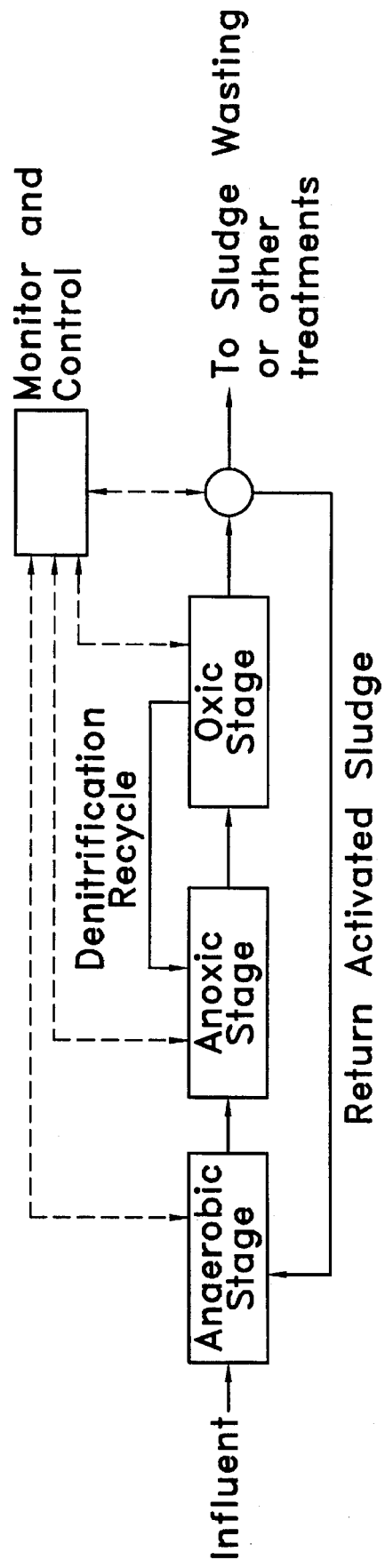
FIG. 4 is a schematic of the monitoring of a typical wastewater treatment process utilizing embodiments of the invention.

The apparatus for monitoring biological activity can be used in all stages of a WWTP or any combination thereof. Incorporation of the apparatus into a typical WWTP is shown schematically in FIG. 4. The general application and use of the apparatus shown in FIGS. 5–10 in the anaerobic, anoxic and/or aerobic stages of a typical wastewater treatment plant will now be discussed.

1. Use in the anaerobic stage

The operational profile of the biological activity monitoring apparatus when installed in the anaerobic stage of a WWTP is illustrated in FIG. 1. The term NFU, as used hereinafter, represents a normalized or relative quantity or level of biological activity. One manner of determining NFU is by detecting NADH fluorescence. Three parameters, $\Delta NFU_1$, $\Delta NFU_2$, and $\Delta t_1$ are analyzed for the evaluation of the biological activity of the microorganisms. $\Delta NFU$ represents the total increase in NADH concentration; $\Delta NFU_1$ represents the first step increase of biological activity; $\Delta NFU_2$ represents the second step increase of biological activity; and $\Delta t_1$ represents the time period of the anoxic portion during the anaerobic stage of the WWTP. The overall change in biological activity through the aerobic, anoxic and anaerobic states of the mixed liquor from the anaerobic stage of treatment can be expressed according to the equation:

$$\Delta NFU = \Delta NFU_1 + \Delta NFU_2$$

$\Delta NFU$ is proportional to the overall biomass concentration in the sample. Although the absolute value of the biomass concentration cannot be determined from a single measurement, it is possible to accurately and reliably estimate the population distribution of the denitrifying and non-denitrifying microorganisms by methods known in the art. When the concentration of dissolved oxygen in the sample decreases to below a critical value and is finally depleted, those microorganisms that cannot use nitrate and/or nitrite as electron acceptors switch to an anaerobic state, shifting the mixed liquor from an aerobic to an anoxic state. This corresponds to the first biological activity increase, $\Delta NFU_1$. The majority of microorganisms which cannot perform denitrification are autotrophic nitriflers, such as *Nitrosomonas* and *Nitrobacter*. Therefore, the value of $\Delta NFU_1/\Delta NFU$ is proportional to the percentage of nitriflers in the overall biomass population. Conversely, those microorganisms that are capable of performing denitrification consume all the nitrate in the sample before entering an anaerobic state.

The second step increase in biological activity, $\Delta NFU_2$, from the sample corresponds to a shift in the sample from an anoxic to an anaerobic state. Therefore, the value of $\Delta NFU_2/\Delta NFU$ is proportional to the percentage of denitrifiers in the overall biomass population.

One possible application of the biological activity monitoring apparatus in the anaerobic stage of a WWTP is to determine the efficiency of $NH_3$ removal. When the value of $\Delta NFU_1/\Delta NFU$ is below a predetermined value, the population of nitriflers in the bioreactor tank is lower than the required amount for proper $NH_3$ removal. Changing operational parameters, such as increasing hydraulic retention time or increasing the RAS flow rate, for example, is helpful in modifying the process to make the WWTP more efficient. If the alteration of the return activated sludge (RAS) flow rate parameter is adopted, it should be continued until the value of $\Delta NFU_1$ reaches a set point so that the population of nitriflers is large enough to maintain the proper nitrification rate.

$\Delta t_1$ is the time the mixed liquor spends in the denitrification stage before the sample shifts to the anaerobic state. When $\Delta t$ represents the hydraulic retention time of the mixed liquor in the anaerobic stage of bioreactor tank 1, then the ratio of $\Delta t_1/\Delta t$ indicates that a fraction of the bioreactor is used for denitrification within the whole anaerobic stage in the WWTP.

2. Use in the Anoxic Stage

Figure 2:
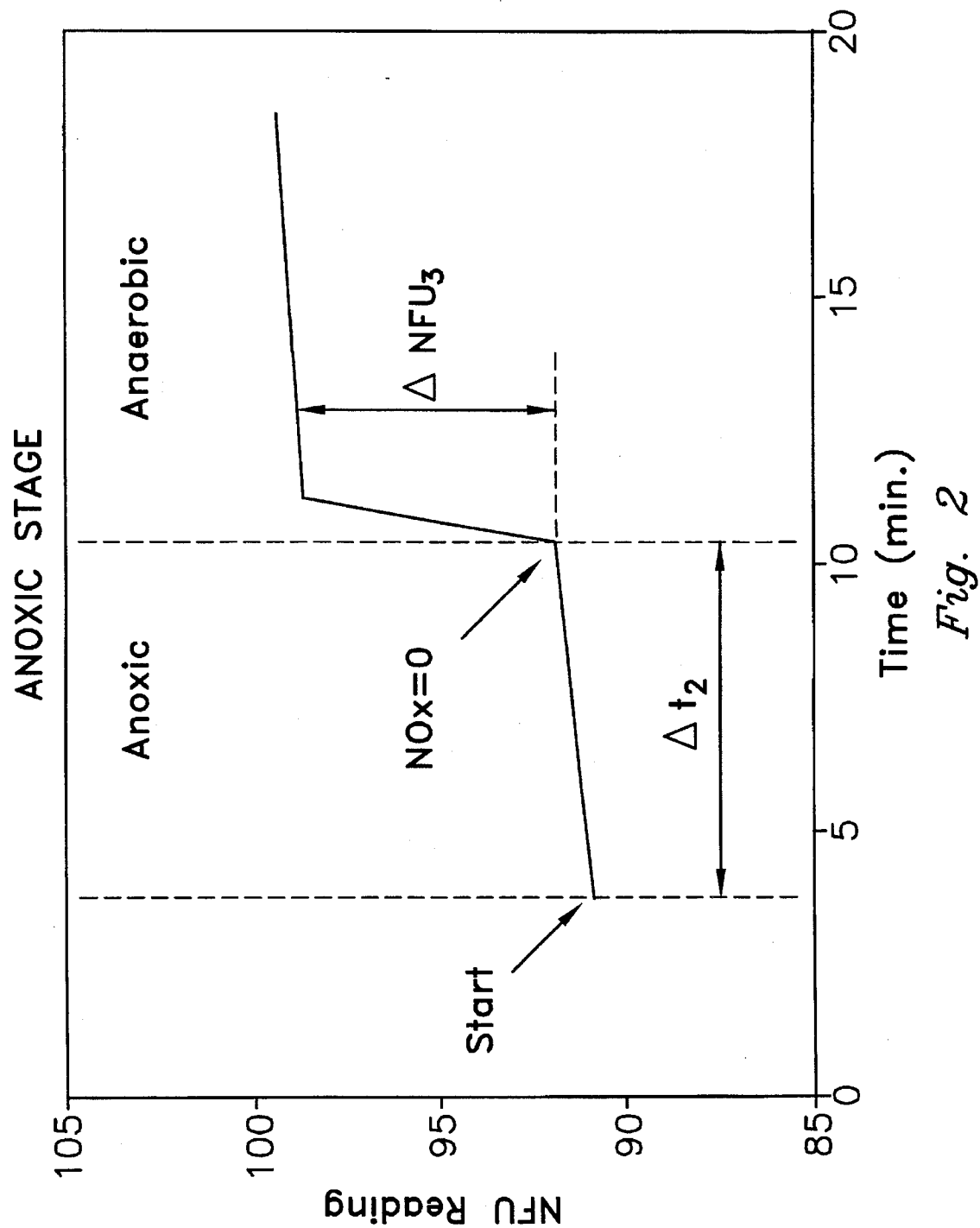
FIG. 2 is a graph of an operational profile depicting changes in biological activity over time from an anoxic stage of treatment.

The operational profile of the biological activity monitoring apparatus when used in the anoxic stage of a WWTP is illustrated in FIG. 2. Two parameters, $\Delta NFU_3$, which represents the change in biological activity during the shift of anoxic to anaerobic state of the sample, and $\Delta t_2$, which represents the length of time in minutes of the anoxic state of the sample, are useful in monitoring and controlling the anoxic stage of a WWTP.

The value of $\Delta t_2$ is measured as the time period from capture of the sample in detector chamber 8 to the moment when denitrification is completed. The value of $\Delta t_2$ can be used to evaluate whether the hydraulic retention time in the whole anoxic stage, $T_{den}$, is long enough for the denitrification process to be completed. The ideal time is $T_{den}=\Delta t_2$. To approach this ideal denitrification time, the internal recycling rate can be adjusted accordingly.

3. Use in the Oxic Stage

Figure 3:
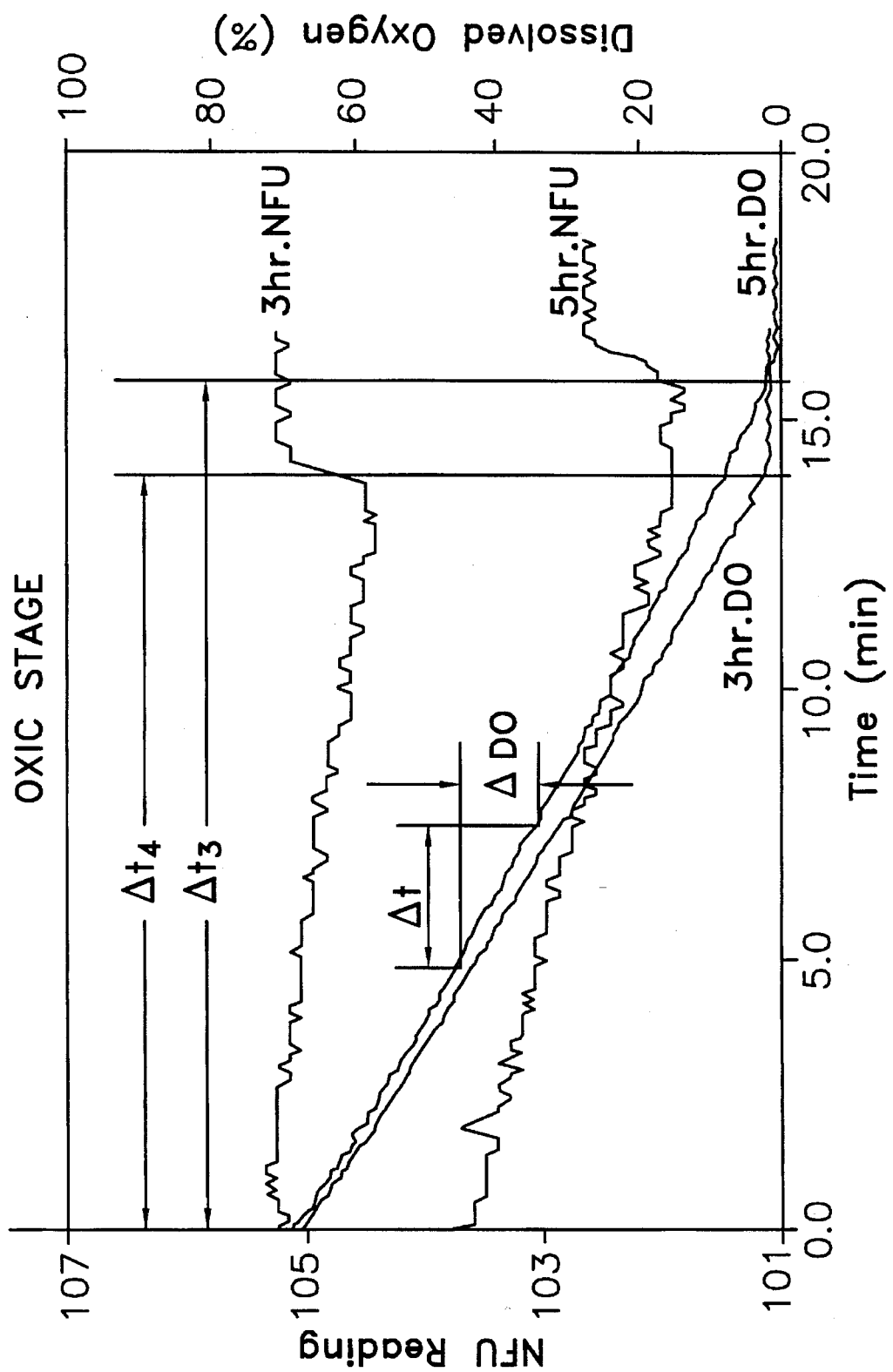
FIG. 3 is a graph of an operational profile depicting the changes in biological activity, measured by fluorescence and dissolved oxygen, over time from an oxic stage of treatment.

An operation profile for the use of the apparatus at the end of the oxic stage of a WWTP is illustrated in FIG. 3. Since the degradation of pollutants is almost completed, the BOD concentration is very low, and the change in biological activity corresponding to the metabolic shift of the captured sample from an aerobic to an anoxic state is very small, but nevertheless detectable.

One of the applications of the invention in the oxic stage is to serve as a $NH_3$ meter. This aspect preferably operates as follows: Two sets of monitoring apparatus (not shown) may be used in the same location in bioreactor tank 10. Both detection chambers 8 (or one detection chamber 8 if both a D.O. and fluorescence probe are employed together as shown in FIGS. 8 and 9) are filled with mixed liquor samples at the same time. For the first chamber, $\Delta t_3$ represents the time from capturing the sample to the start of the anoxic state of the sample registered by computer 13. In the second chamber, immediately after the chamber is filled with mixed liquor, a certain amount of $NH_3$ is added so that the $NH_3$ concentration change in detection chamber 8 is known, for example 0.5 ppm, from the feeding device 11. The time, $\Delta t_4$, from capturing the sample in chamber 8 to the start of the anoxic state of the wastewater in the detection chamber 8 is then registered.

In order to determine the $NH_3$ concentration, it is assumed that the D.O. consumption in the oxic stage is mostly due to the nitrification process. A typical operational profile for the consumption of dissolved oxygen during the oxic stage is illustrated in FIG. 3. Experimental results performed indicate that the oxygen consumption rate of the mixed liquor changes negligibly when acetate and glucose (5 ppm) are added to the system with feeding device 11, while significant change was observed when 0.1 ppm of $NH_3$ was added to the system.

The concentration of $NH_3$ in the oxic state of the WWTP is expressed as:

$$(NH_3)_1 = \Delta NH_3 \Delta t_4 / (\Delta t_3 - t_4)$$

Where $(NH_3)_1$ is the ammonia concentration in the water phase at the end of the oxic stage, $\Delta NH_3$ is the known amount of ammonia added to the second detection chamber, respectively. The invention can accordingly be used in the oxic state of a WWTP to accurately monitor the $NH_3$ concentration in the bioreactor tank. Various system parameters, such as retention time, can then be altered to enhance the nitrification process and, if necessary, to increase the efficiency of the waste water treatment system.

Application of the apparatus with a D.O. probe 10 in the oxic stage in a wastewater treatment plant is described as follows: When sample chamber 8 is filled with fresh wastewater (mixed liquor), the concentration of dissolved oxygen is measured by the D.O. probe. Depending on the initial D.O. concentration, air may be supplied to sample chamber 8 through an air diffuser 103 installed inside chamber 8 to increase the D.O. concentration higher than a preset value.

When aeration is off, the concentration of D.O. decreases due to the biological oxygen consumption of the wastewater (mixed liquor). Within a period of time $\Delta t$, the decrease in concentration of dissolved oxygen can be expressed as $\Delta D.O.$ The biological oxygen consumption rate (BOCR) is measured as $$BOCR = \frac{\Delta D.O.}{\Delta t}$$

Knowing the biological oxygen consumption rate (BOCR) gram(liter-hour)$^{-1}$, and the initial concentration of dissolved oxygen $(D.O._{ini})$ gram liter$^{-1}$, in sample chamber 8, which is also the concentration of D.O. in the wastewater treatment tank at the moment when a sample is taken in, the air supply rate ASR, gram.hour$^{-1}$, to the wastewater treatment tank with volume of V, can be calculated as $$ASR = \left[ BOCR + \frac{D.O_{ini}}{\Delta t} \right] \cdot V$$

The value of ASR is useful information for the control of air or oxygen usage. Air blowers are frequently a major power consumption source in wastewater treatment plants.

When the concentration of dissolved oxygen decreases below a critical value, the wastewater (mixed liquor) reaches an anaerobic state, or anoxic state if nitrate and/or nitrite is present. The transition point can be detected by both an NADH probe and a D.O. probe. The total time from the moment when aeration is off to the transition point is registered as biological oxygen consumption time (BOCT). For a given D.O. concentration and wastewater (mixed liquor), the biological oxygen consumption time is dependent on the nutrients left in the wastewater. A lower amount of nutrients in the wastewater results in less D.O. consumed by the wastewater (mixed liquor), which results in a long biological oxygen consumption time. Thus, BOCT is directive to the degree of nutrient removal in the wastewater and can be used to check the efficiency of the treatment process.

In the method according to the invention, information about biomass composition, efficiency of denitrification, nitrification and BOD removal processes and $NH_3$ concentration in the oxic stage of a WWTP can be obtained. This information may be monitored and analyzed by computer 13 which evaluates the biological activity in the anaerobic, anoxic and aerobic stages of a WWTP and can alter system parameters such as the RAS flow rate, the oxygen supply rate, the internal recycling rate or the hydraulic residence time or the like to maximize the efficiency of the WWTP in response to transient conditions or normal operation.

Although the invention has been illustrated by use of specific embodiments thereof, it should be noted that a wide variety of equivalents may be substituted for the specific elements and steps shown and described without departing from the spirit or scope of this invention as defined in the appended claims. For example, the present invention can be used to monitor various parameters of the individual aerobic, anoxic and anaerobic stages of a wastewater treatment plant individually, or the invention can be used to monitor and control the entire WWTP operation in maximizing the efficiency thereof. Additionally, individual components of the invention may utilize equivalent substitutions. For example, the sample in detection chamber 8 may be uniformly suspended or distributed by use of any means of controllable agitation. The monitoring system may consist of a personal computer with applicable software or individual electronic meters to be analyzed separately, all of which are known in the art. It should also be emphasized that although emphasis has been placed on measurement of dissolved oxygen with a "probe" to determine the quantity or concentration of oxygen, this emphasis is simply the preferred manner in which oxygen quantity or concentration is determined. Other means and methods for accomplishing this task are fully contemplated as falling within the scope of this invention. Still other means known and not yet developed can be used so long as they are capable of determining the presence of oxygen in the wastewater.

What is claimed is:

1. Apparatus for in situ monitoring biological activity in a wastewater treatment process comprising:
    a wastewater sample chamber immersed in a supply of wastewater and having an opening;
    a closure positioned adjacent said opening and adapted to substantially seal said chamber;
    a probe positioned relative to said sample chamber to detect changes in dissolved oxygen content in samples of wastewater in said chamber;
    a dissolved oxygen analyzer connected to said probe; and
    a controller connected to said analyzer and said closure to introduce and remove samples from said chamber at selected time intervals.

2. The apparatus of claim 1 further comprising a storage device connected to said probe for registering changes in dissolved oxygen detected by said probe.

3. The apparatus defined in claim 2 wherein said storage device, said analyzer and said controller comprise a computer.

4. The apparatus defined in claim 1, further comprising a sample agitator located interiorly of said chamber.

5. The apparatus defined in claim 4, wherein said agitator comprises a mechanical stirrer.

6. The apparatus defined in claim 5 wherein said stirrer is operated by a motor.

7. The apparatus defined in claim 4 wherein flow of fluids into and out of said chamber is assisted by said agitator when said closure is in an open position.

8. The apparatus defined in claim 7 wherein said closure is adapted to move toward and away from said opening.

9. The apparatus defined in claim 8 further comprising at least one opening/closing member connected to said closure and adapted to move relative to said chamber.

10. The apparatus defined in claim 9 further comprising 1) a spring connected to said opening/closing member to apply substantially constant closing force to said closure relative to said opening and 2) a solenoid connected to said opening/closing member to actuate opening force to said closure relative to said opening sufficient to overcome the closing force of said spring.

11. The apparatus defined in claim 9 further comprising 1) a spring connected to said opening/closing member to apply substantially constant closing force to said closure relative to said opening and 2) a motor connected to said opening/closing member to actuate opening force to said closure relative to said opening sufficient to overcome the closing force of said spring.

12. The apparatus defined in claim 1, wherein said closure connects to a motor.

13. The apparatus defined in claim 12, wherein said closure moves toward said opening when said motor rotates in a first direction and moves away from said opening when said motor rotates in a second direction.

14. The apparatus defined in claim 12 further comprising a mechanical stirrer connected to said motor, said stirrer adapted to operate when said closure seals said chamber in a closed position and/or when said closure is in an open position.

15. Apparatus for in situ monitoring biological activity in a fluid treatment process comprising:
    a fluid sample chamber immersed in a fluid supply undergoing treatment, said sample chamber having an opening to permit ingress and egress of fluid;
    a cover positioned to move toward and away from said opening;
    a fluid agitator positioned with the sample chamber;
    a dissolved oxygen probe having a detection end positioned interiorly of the sample chamber;
    a dissolved oxygen analyzer connected to said probe; and
    a controller connected to said analyzer and said cover to introduce and remove samples from said sample chamber at selected time intervals.

16. The apparatus defined in claim 15 further comprising:
    a radiation source positioned relative to said chamber to irradiate fluid in said chamber with radiation of a selected wavelength;
    a detector positioned relative to fluid in said chamber to detect changes in fluorescence emitted by NADH in microorganisms within fluid in said chamber in response to said radiation;
    an NADH analyzer connected to said detector and said controller.

17. Apparatus for in situ monitoring and controlling biological activity in a wastewater treatment process comprising:
    a wastewater sample container submerged in a wastewater supply undergoing treatment, said sample container having a wastewater opening;
    a cover positioned to open and close said opening;
    a wastewater distributor located within the sample container;
    a probe having a detection end positioned interiorly of the sample container;
    a biological activity analyzer connected to said probe; and
    a process controller connected to 1) said analyzer and said cover to introduce and remove samples from said container at selected time intervals and 2) one or more process parameter controllers.

18. The apparatus defined in claim 17 wherein said process parameter controllers control parameters selected from the group consisting of rate of input of primary influent, rate of input of return activated sludge, rate of denitrification recycle, type and quality of microorganisms, number and location of anaerobic, anoxic and aerobic stages, residence times in said anaerobic, anoxic and aerobic stages, nutrient type and introduction rate, air or oxygen purity and introduction rate, pH and temperature.

19. The apparatus defined in claim 18 wherein said probe is a dissolved oxygen detection probe.

20. The apparatus defined in claim 19 wherein said analyzer analyzes dissolved oxygen content of samples in said container.

* * * * *